United States Patent
Dileo

[11] 3,985,022
[45] Oct. 12, 1976

[54] ULTRASONIC THICKNESS MEASURING METHOD AND APPARATUS

[75] Inventor: Christopher C. Dileo, Brewster, N.Y.; Richard J. Pittaro, Stamford, Conn.

[73] Assignees: Krautkramer-Branson, Incorporated, Stratford, Conn.

[22] Filed: June 9, 1975

[21] Appl. No.: 584,778

[52] U.S. Cl. .............................. 73/67.8 R; 73/67.9
[51] Int. Cl.² .................. G01N 29/00; G01N 29/04
[58] Field of Search ................. 73/67.7, 67.8 R, 67.9

[56] References Cited
UNITED STATES PATENTS

| | | | |
|---|---|---|---|
| 3,354,700 | 11/1967 | Schindler | 73/67.9 |
| 3,427,868 | 2/1969 | Charbonnier | 73/67.9 |
| 3,605,504 | 9/1971 | Kummer et al. | 73/67.9 |
| 3,688,565 | 9/1972 | Brech | 73/67.9 |

FOREIGN PATENTS OR APPLICATIONS

| | | | |
|---|---|---|---|
| 20,229 | 7/1970 | Japan | 73/67.8 R |

Primary Examiner—James J. Gill
Attorney, Agent, or Firm—Ervin B. Steinberg; Philip J. Feig

[57] ABSTRACT

The invention refers to an ultrasonic measuring means exhibiting improved stability and calibration adaptability. Ultrasonic energy signals are transmitted into a workpiece and echo responsive signals are received therefrom. A timing signal having a pulse width commensurate with the workpiece thickness is generated. The pulse width is measured by a time interval averaging circuit in combination with a programmable counting means for adjusting the quantity of time interval average measurements required for determining the thickness of the workpiece. The programmable means is adjusted to a value commensurate with the acoustic velocity of the workpiece for causing the output of the apparatus to display the dimension of the workpiece measured.

32 Claims, 3 Drawing Figures

ULTRASONIC THICKNESS MEASURING METHOD AND APPARATUS

BRIEF SUMMARY OF THE INVENTION

This invention refers to an ultrasonic thickness measuring arrangement exhibiting improved stability and calibration adaptability. More specifically, this invention concerns an ultrasonic pulse-echo thickness measuring method and apparatus comprising a time interval averaging circuit in combination with a programmable means for adjusting the quantity of time interval average measurements required for determining the thickness of a workpiece.

Measuring the thickness of a workpiece by ultrasonic energy is well known. The general measurement method comprises the steps of coupling an ultrasonic transmit-receive probe to the surface of the workpiece, periodically transmitting an ultrasonic search pulse into the workpiece and subsequently receiving echo responsive pulses produced as a respective search pulse encounters the entrant surface and the rear wall of the workpiece. A timing gate circuit is started responsive to the receipt of the entrant surface responsive echo pulse and is terminated upon receipt of the rear wall responsive echo pulse. The time interval between the receipt of the two mentioned pulses, i.e. the width of the produced timing signal, is responsive to the workpiece thickness.

The method of determining the workpiece thickness value from the timing signal pulse width has presented difficulties in the prior art apparatus. Specifically, when using analog circuits to determine the thickness a constant current generator and a ramp generator are required, see for instance U.S. Pat. No. 3,485,087, issued to K. Brech. Such an arrangement has led to problems in maintaining stable linearity of the ramp waveform with varying operating temperature and aging of the electronic circuit components. The usual method of generating the ramp waveform is to charge a capacitor with constant current during the interval corresponding to the width of the timing signal. The capacitor integrates the constant current as function of time, thereby generating a ramp voltage waveform. The peak value of the ramp voltage is indicative of the width of the timing signal. The stability of the current source and the capacitor vary over the normal operating temperature range thereby affecting the stability and accuracy of the thickness measurement.

In other prior apparatus, a digital circuit is used which provides improved drift and stability characteristics in comparison with the analog circuits, but requires the use of a stable high frequency clock. The high frequency clock tends to produce noise in the circuit and consume excessive power. In order to obtain a thickness resolution of 0.001 inch (0.03 mm) when measuring an aluminum workpiece a clock having a frequency of 125 MHz is required. Moreover, for measuring the thickness of workpieces having different sound velocities, the clock frequency must be changed correspondingly and expensive tuning components exhibiting stable characteristics over a certain temperature range are required. Alternatively, a plurality of high frequency clocks, each oscillating at a different frequency, are required for measuring the thickness of materials having different sound velocities.

Other prior systems employ a vernier counting method using two stable, accurate and expensive clock circuits. The method of vernier counting is described in the book "Pulse, Digital and Switching Waveforms" by Millman and Taub, McGraw-Hill, New York, 1965, pp. 683–687.

Time interval averaging is used in certain prior apparatus for increasing the stability and the resolution capability of the thickness measurement. A timing signal having a pulse width responsive to the workpiece thickness is generated as described above. The pulse width is measured by counting the quantity of pulses (P) from a high frequency clock occurring during the timing signal interval, dividing the quantity of pulses by a constant N to obtain the average quantity of pulses per measurement (P/N). The quantity of measurements performed (N') typically is made equal to N for obtaining the average quantity of clock pulses counted during the timing gate interval ($\overline{P}$) which is:

$$\overline{P} = \frac{P}{N} \times N' \qquad \text{(eq. 1)}$$

The time interval averaging method improves resolution as compared with the digital measuring method and also provides increased stability by averaging the always present white noise to zero. The time interval averaging system while providing these advantages is not adapted to be calibrated since the quantity of measurements N' in the numerator of the equation 1 is fixed. In order to maintain the same resolution when measuring workpieces having different acoustic velocities, a separate clock or an adjustable clock is required for each different acoustic velocity, resulting in an expensive and complex apparatus.

In the present apparatus, a modification of the time interval averaging circuit of the type described above is used. A programmable counting means, for example a programmable divide by N counter circuit, is provided for calibrating the apparatus for measuring the thickness of workpieces having different acoustic velocities. In a preferred embodiment the programmable counter is programmed by suitable means, such as thumb wheel switches, to a value commensurate with the acoustic velocity of the workpiece. The quantity of measurements (Q) is equal to the value programmed into the programmable counter. The quantity of pulses occurring during the timing gate interval is:

$$\overline{P} = \frac{P}{N} \times Q \qquad \text{(eq. 2)}$$

The timing signal pulse width is equal to the time required for an ultrasonic signal traveling at a velocity V to traverse twice the workpiece thickness, 2 x thickness/V. The quantity of clock pulses per unit of time is equal to the clock frequency $f$. The fixed value N for obtaining the average quantity of pulses per measurement remains unchanged an equation 2 above becomes:

$$\overline{P} = \frac{2 \times \text{thickness} \times f \times Q}{V \times N} \qquad \text{(eq. 3)}$$

When the quantity of measurements performed (Q) as determined by the programmable counter is equal to the acoustic velocity (V) of the workpiece equation 3 reduces to:

$$\overline{P} = \frac{2 \times \text{thickness} \times f}{N} \qquad \text{(eq. 4)}$$

If the frequency $f$ and the frequency divider $N$ are selected to be in the ratio of $5 \times 10^{(n-1)}$, where the exponent $(n-1)$ is dependent upon the magnitude of the frequency $f$ and the frequency divider $N$ then equation 4 is further reduced to:

$$\overline{P} = \text{thickness} \times 10^n \qquad (5)$$

It will be apparent that after proper decade division the quantity of pulses counted is equal to the thickness of the workpiece. When the ratio is other than $5 \times 10^{(n-1)}$ additional scaling circuits, well known in the art, are used for converting the counted quantity of pulses ($\overline{P}$) into a thickness measurement reading.

The thickness measuring apparatus can readily be calibrated for measuring the thickness of any workpiece. If the acoustic velocity of the workpiece is unknown, a sample of the workpiece having a known thickness is measured. The programmable counting means is adjusted until the measured thickness displayed equals the known thickness.

The apparatus described comprises the advantages of the prior art devices without the disadvantages. Since the apparatus employs digital circuits the disadvantages inherent in analog constant current generators and ramp generators are obviated. The programmable means which varies the quantity of measurements before displaying the thickness value makes it possible to use a single clock at a fixed frequency, wherein the frequency of the clock is lower than that used in prior digital measuring apparatus. The thickness measuring apparatus in accordance with the present invention can be used for measuring the thickness of workpieces having different acoustic velocities without the necessity for changing the clock frequency. Moreover the hertofore troublesome problems of stability and drift are eliminated.

A principal object of this invention, therefore, is the provision of an ultrasonic thickness measuring apparatus comprising a programmable means for use with a time interval averaging circuit.

Another principal object of this invention is the provision of an ultrasonic thickness measuring apparatus including means for calibrating the apparatus for measuring workpieces having different acoustic velocities.

A further object of this invention is the provision of a digital ultrasonic thickness measuring apparatus having programmable means for providing an apparatus characterized by ease of calibration for any desired sound velocity of the workpiece and increased stability and resolution.

Further and still other objects of this invention will become more readily apparent when considering the following specification in conjunction with the accompanying drawing.

DETAILED DESCRIPTION OF THE INVENTION

Figure 1:
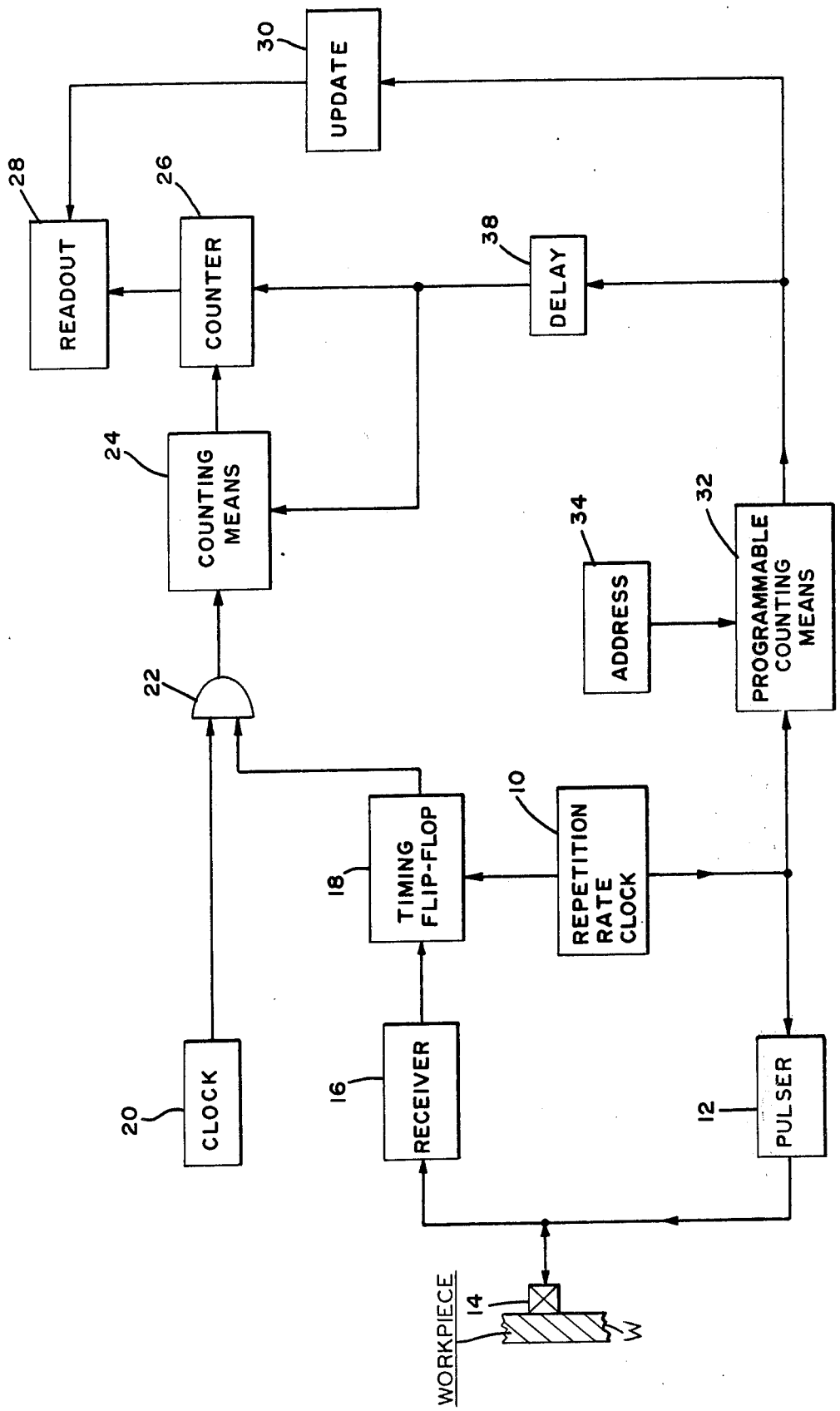
FIG. 1 is an electrical schematic block diagram of a preferred embodiment of the ultrasonic thickness measuring apparatus in accordance with the present invention.

Referring to the figures and FIG. 1 in particular, there is shown a schematic block diagram of a preferred embodiment of the invention. A repetition rate clock 10 cyclically provides timing pulses, typically at a frequency in the range between 500 Hz and 20 kHz, to a pulser 12 for cyclically energizing the transmit-receive probe 14. The transmit-receive probe 14 responsive to the electrical signal from the pulser 12 periodically transmits an ultrasonic search pulse into a workpiece W whose thickness is to be measured and receives echo responsive pulses. These echo responsive pulses are converted by the probe to electrical signals and fed to a receiver circuit 16 which provides echo responsive trigger signals to the timing flip-flop 18 for generating a thickness responsive timing signal which corresponds to the transit time of a respective search pulse through the workpiece. There is one timing signal produced for each search pulse provided from the probe 14.

A clock 20 provides a train of pulses to a gate circuit 22 at a predetermined frequency. The timing signal from the flip-flop 18 causes the gate circuit 22 to be open to a time interval commensurate with the width of the timing signal which corresponds to the thickness of the workpiece W. Counting means 24, in a preferred embodiment a fixed divide by N counter circuit, is coupled to the output of the gate circuit 22 for accumulating the quantity of pulses received from the clock 20 via the open gate 22 during a respective timing signal interval and for providing an output count signal indicative of the accumulated quantity of pulses divided by N. A counter 26 coupled to the counting means 24 accumulates and stores the output count signals from the fixed divide by N counting means 24. The quantity of pulses accumulated in the counter 26 is provided to a readout device 28 responsive to the transmission of an update signal from the update circuit 30 to the readout device 28. While in the preferred embodiment the counting means 24 is a fixed divide by N counter circuit, any combination of counting circuits and logic circuits may be used in which the output count is increased after the receipt by counting means 24 of N clock pulses transmitted from clock 20 via the open gate circuit 22.

Programmable counting means 32, in a preferred embodiment a programmable divide by N counter, is preset by address means 34, such as thumb wheel switches or other suitable adjusting means, to the acoustic velocity of the workpiece whose thickness is to be measured. To test an aluminum workpiece having an acoustic velocity of $2.5 \times 20^5$ inch/sec ($6.35 \times 10^5$ cm/sec), for example, the thumb wheel switches are set to an index reading 2500 for measuring the thickness of the workpiece in American units or alternatively the thumb wheel switches are set to an index reading 6350 for measuring the thickness of an aluminum workpiece in metric units. The counting means 32 counts the quantity of timing pulses transmitted from the clock 10 to the pulser 12 and, hence, the quantity of timing signal intervals.

When the quantity of timing pulses from the clock 10 counted by the programmable counting means 32 is equal to the preset number in the address means 34, a signal is transmitted from the counting means 32 to the update circuit 30 and to the delay circuit 38. The readout now updates its indication by receiving the count from the counter 26. After a delay sufficient to ensure that the update signal is received by the readout 28, a reset signal is transmitted from delay 38 to the counting means 24 and to the counter 26 for resetting both circuits to zero. The counting means 32 also resets itself for cyclic operation upon counting the preset quantity of timing pulses.

DESCRIPTION OF OPERATION

For measuring the thickness of a workpiece, the transmit-receive probe 14 is coupled for ultrasonic energy transfer to the surface of a workpiece W by means of a suitable couplant, such as oil or water. The velocity of the workpiece is programmed into the programmable divide by N counting means 32 by the address means 34, such as thumb wheel switches.

The periodically generated timing pulse conducted from the repetition rate clock 10 to the pulser 12 causes the pulser to periodically energize probe 14. Responsive to each applied pulse signal the probe 14 transmits an ultrasonic energy search pulse into the workpiece and receives corresponding echo pulses from the entrant surface and the rear wall of the workpiece. The received echo pulses are converted by the probe 14 into electrical signals and conducted to the receiver 16. The receiver 16 provides output trigger signals to the timing flip-flop circuit 18. A timing pulse is also conducted from the clock 10 to the timing flip-flop 18 for resetting the timing flip-flop 18 at the beginning of each cycle. The video output trigger pulse obtained from the receiver 16 and corresponding to the entrant surface responsive echo pulse starts the timing flip-flop circuit 18, and the video output trigger pulse corresponding to the rear wall responsive echo stops the timing flip-flop circuit 18. The pulse width of the resultant output timing signal is responsive to the distance traveled by the ultrasonic pulse signal through the workpiece during the time interval between the trigger signals, i.e. the workpiece thickness.

The resultant timing signal from the timing flip-flop circuit 18, having a pulse width commensurate with the thickness of the workpiece, is conducted to one input of the gate 22 for opening the gate 22 during the interval when the timing signal is present. The clock 20 provides discrete clock pulses to the other input of gate 22. The clock pulses in a preferred embodiment are at a frequency of 12.8 MHz which frequency is much higher than the frequency of the repetition rate clock 10, typically 10 kHz. During the timing signal interval when the gate 22 is open, the clock pulses from the clock 20 are conducted via the open gate 22 to the fixed divide by N counting means 24. The counting means 24 provides an output count signal upon the receipt of every N pulses from the clock 20. The value of N in the embodiment shown is chosen to cause the ratio of the clock 20 frequency in megahertz divided by the number N to equal 0.05. In the present example wherein the clock frequency is chosen at 12.8 MHz, the number N is selected to be 256.

It will be apparent that the timing signal from timing flip-flop is asynchronous with the clock pulses from clock 20. In other words, the opening and the closing of the timing gate is not coincident with the clock pulses from the clock 20. The quantity of counts counted by the counting means 24, therefore, will vary for each timing signal depending upon the point in time at which the timing signal occurs vis-a-vis the clock pulses from clock 20. The counting means 24 provides a single output count signal for each N pulses during a respective timing signal interval and conducts the output count signals to counter 26 which accumulates the counts obtained from counting means 24.

After a predetermined quantity of measurements have been made, i.e. a predetermined quantity of timing signals from the flip-flop circuit 18 have been obtained as programmed by the counting means 32 via address means 34, a signal from the counting means 32 is provided to update circuit 30. The update circuit 30 responsive to the signal from counting means 32 transmits an update signal to the readout device 28 for displaying the thickness of the workpiece which is commensurate with the number of counts accumulated and stored in counter 26. The readout device 28 stores the display until the next succeeding update signal. The output signal from counting means 32 is delayed by delay means 38 for a period of time sufficient to cause the readout device 28 to be updated to the value in the counter 26 after which time a signal is conducted from the delay circuit 38 to the fixed divide by N counting means 24 and to the counter 26 for resetting both devices.

One of the main features of the invention is the method of calibrating the thickness measuring device. In the foregoing description the acoustic velocity of the workpiece was known and programmed directly into the programmable divide by N counting means 32 via the address means 34. In other applications the velocity of the ultrasonic signal through the workpiece is unknown. In such a case, a sample of the workpiece of known thickness is ultrasonically coupled to the probe 14. The address means 34 associated with programmable counting means 32 then is adjusted for causing the readout device 28 to display a value corresponding to the known thickness. The readout may be in American units (inches) or in metric units (centimeters) but once the adjustment is performed the address means 34 need not be readjusted when measuring a workpiece having the same sound velocity but unknown thickness. In prior art ultrasonic thickness measuring devices using time averaging the number of measurements (the update period) has been maintained constant. In these devices the repetition rate or the clock frequency has been varied requiring the use of expensive tuned clock circuits to change the frequency. In the present embodiment the quentity of measurements performed is programmable for providing a method of calibrating the apparatus. The use of digital circuitry combined with a means for calibrating the apparatus results in an ultrasonic thickness measuring apparatus exhibiting improved stability, accuracy and resolution in comparison with the apparatus known heretofore.

Figure 2:
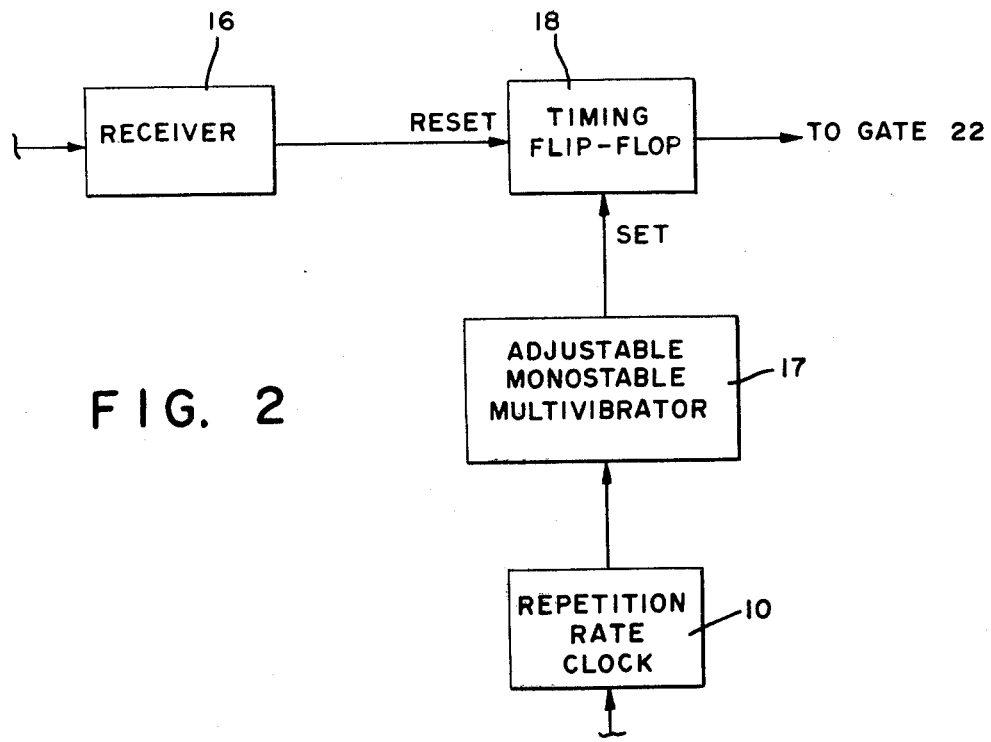
FIG. 2 is an electrical schematic block diagram of an alternative embodiment of a portion of the invention per FIG. 1.

In the foregoing description the start of the timing gate from timing flip-flop 18 is triggered by a signal responsive to the entrant surface responsive echo pulse. It will be apparent as shown in FIG. 2; that the start trigger signal may be generated also electronically from an adjustable monostable multivibrator 17 coupled from the repetition rate clock 10 to the timing flip-flop circuit 18. The pulse width of the multivibrator is adjusted to provide a trigger signal to the timing flip-flop 18 circuit delayed by the interval between the generation of the timing signal by clock 10 and the ultrasonic search pulse of the probe entering the workpiece. The use of an artificial start trigger signal obviates the requirement for a suppression means for damping the ringing of the probe 14 during the anticipated time of receipt of an entrant surface responsive echo signal. This problem is particularly acute when the probe is in direct contact with the surface of the workpiece and the time from the timing pulse to the start of the timing signal from timing flip-flop 18 corresponds to the time required for an ultrasonic signal to travel through a relatively thin wear plate disposed on the front of probe 14.

Figure 3:
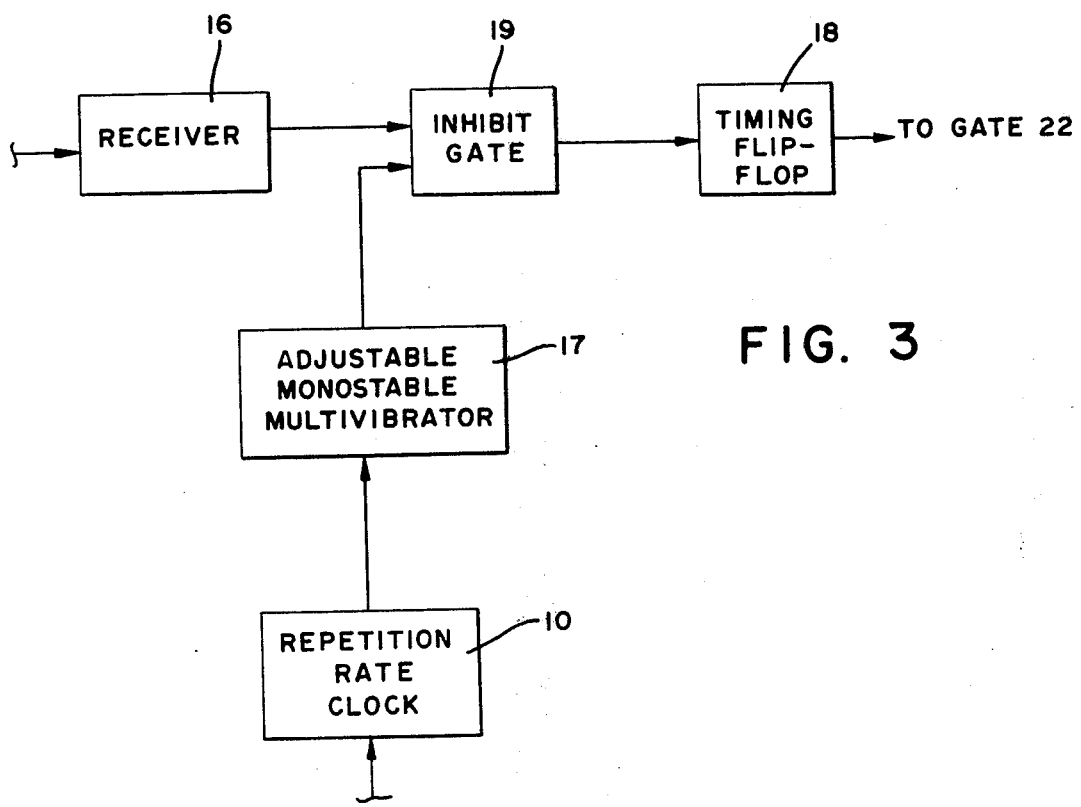
FIG. 3 is an electrical schematic block diagram of another alternative embodiment of a portion of the invention per FIG. 1.

In an alternative embodiment the counting means and/or the timing means is inhibited for a fixed period of time after the transmission of a search pulse into the workpiece by an inhibit gate 19 coupled as shown in FIG. 3 to the receiver 16 as is known in the art for causing the timing flip-flop circuit 18 to be responsive only to a pair of echo signals arising from rear wall reflections received after the entrant surface responsive echo signal. It is, of course, possible to measure the time interval between two non-consecutive rear wall echo pulses as is known in the art. It will be apparent that in either embodiment the count in the counter 26 must be divided by the proper divisor.

While it is most advantageous to provide an address means which is programmed to indicate by means of indicia the acoustic velocity of the workpiece, it will be apparent that by selecting the ratio of the frequency of the clock 20 and the value N in the counting means 24 to a value other than $5 \times 10^{(n-1)}$ or by employing additional clock and/or counting means within the circuit, the address means 34 can be programmed for any arbitrary units.

In the foregoing description the signal from counter 26 is provided to a digital display readout 28. It will be apparent, however, that the output signal from counter 26 may be provided to other indicating or display means, or to signal processing means. For example, when sorting workpieces the output signal can be coupled to a digital comparator for providing an accept/reject signal when the thickness of the workpiece is between predetermined tolerance levels. The output signal can be provided also to a digital to analog converter whose output is coupled to a strip chart recorder. In other applications, the output signal, without being displayed, can be provided to a computer means for further signal processing and analysis.

While there has been described and illustrated a preferred embodiment of the present invention and several modifications thereof, it will be apparent to those skilled in the art that further modifications and changes may be made without departing from the broad principle of this invention which shall be limited only by the scope of the appended claims.

What is claimed is:

1. The method of measuring the dimension of a workpiece by the ultrasonic pulse-echo method comprising:
    transmitting periodically an ultrasonic search pulse into the surface of the workpiece and receiving an echo pulse responsive to each such search pulse intercepting an acoustic impedance change;
    providing counts commensurate with the transit time of a respective search pulse traversing the workpiece dimension from said surface to the impedance change as determined by the time interval between a first signal responsive to the transmission of such search pulse and the receipt of a second signal responsive to the echo pulse associated with the respective search pulse;
    accumulating the counts provided during successive such time intervals, and
    providing an output signal responsive to said accumulated counts when a predetermined programmable quantity of search pulses has been transmitted, said quantity being commensurate with the acoustic velocity of the workpiece.

2. The method of measuring the thickness of a workpiece as set forth in claim 1, said predetermined quantity of search pulses being programmable by adjustable means.

3. The method of measuring the thickness of a workpiece as set forth in claim 1, said counts being periodic clock pulses.

4. The method of measuring the thickness of a workpiece as set forth in claim 1, said first signal being responsive to the search pulse entering the surface of the workpiece and said second signal beng responsive to said search pulse intercepting the rear wall of the workpiece.

5. The method of measuring the thickness of a workpiece as set forth in claim 1, said first signal being an electrical signal generated a predetermined time after transmitting said search pulse and said second signal being responsive to an echo signal arising from the rear wall of the workpiece.

6. The method of measuring the dimension of a workpiece as set forth in claim 1, said output signal providing a readout of the dimension measured.

7. The method of measuring the dimension of a workpiece as set forth in claim 1, said predetermined quantity being programmable in units of sound velocity.

8. The method of measuring the thickness of a workpiece by the ultrasonic pulse-echo method comprising:
    transmitting periodically an ultrasonic search pulse into the surface of the workpiece and receiving an echo pulse responsive to each such search pulse intercepting an acoustic impedance change;
    providing counts commensurate with the transit time of a respective search pulse traversing the workpiece thickness as determined by the time interval between a first signal being responsive to said search pulse intercepting the rear wall of the workpiece and a second signal being responsive to subsequent reflection of ultrasonic energy provided by said search pulse at the rear wall;
    accumulating the counts provided during successive such time intervals, and
    providing an output signal responsive to said accumulated counts when a predetermined programmable quantity of search pulses has been transmitted, said quantity being commensurate with the acoustic velocity of the workpiece.

9. An apparatus for measuring the dimension of a workpiece which includes circuit means for periodically transmitting an ultrasonic search pulse into the workpiece and subsequently receiving an echo pulse responsive to the transmitting of the search pulse and such search pulse intercepting an acoustic impedance change, means coupled to said circuit means for providing counts commensurate with the transit time of the search pulse traversing the workpiece dimension as determined by a first signal responsive to the transmitting of said search pulse and a second signal responsive to the receipt of the echo pulse, the improvement comprising:

first counting means coupled for receiving said counts and accumulating successive counts responsive to the periodic transmission of search pulses and ensuing transit times, and second counting means coupled to said circuit means and said first counting means for providing an output signal from said first counting means commensurate with the accumulated counts when a predetermined programmable quantity of search pulses has been transmitted, said quantity being commensurate with the acoustic velocity of the workpiece.

10. An apparatus for measuring as set forth in claim 9, including a readout means coupled for receiving said output signal and being conditioned thereby.

11. An apparatus for measuring as set forth in claim 10, said readout means being a digital display.

12. An apparatus for measuring as set forth in claim 9, said second counting means being programmable by adjustable means.

13. An apparatus for measuring as set forth in claim 9, said counts being fixed frequency clock pulses.

14. An apparatus for measuring set forth in claim 13, said accumulated counts occurring during said programmable quantity of search pulses being responsive to the average quantity of said clock pulses occurring between said first and second signals.

15. An apparatus for measuring as set forth in claim 9, and readout means coupled to said first counting means and said second counting means for displaying said accumulated counts responsive to an update signal provided by said second counting means in response to said predetermined quantity of search pulses.

16. An apparatus for measuring as set forth in claim 9, said first signal being responsive to said search pulse entering the workpiece and said second signal being responsive to said search pulse intercepting the rear wall of the workpiece.

17. An apparatus for measuring as set forth in claim 9, said first signal being responsive to the echo signal from the entrant surface of the workpiece and said second signal being responsive to the echo from the rear wall of the workpiece.

18. An apparatus for measuring the thickness of a workpiece which includes circuit means for periodically transmitting an ultrasonic search pulse into the workpiece and subsequently receiving an echo pulse responsive to the search pulse intercepting an acoustic impedance change, means coupled to said circuit means for providing counts commensurate with the transit time of the search pulse traversing the workpiece thickness as determined by a first signal being responsive to said search pulse intercepting the rear wall of the workpiece and a second signal being responsive to ultrasonic energy provided by said search signal subsequently intercepting the rear wall of the workpiece, the improvement comprising:

first counting means coupled for receiving said counts and accumulating successive counts responsive to the periodic transmission of search pulses and ensuing transit times, and second counting means coupled to said circuit means and said first counting means for providing an output signal from said first counting means commensurate with the accumulated counts when a predetermined programmable quantity of search pulses has been transmitted, said quantity being commensurate with the acoustic velocity of the workpiece.

19. An ultrasonic apparatus for measuring a dimension of a workpiece by periodically transmitting a search pulse into the workpiece and subsequently receiving an echo pulse responsive to the transmission of the search pulse, the combination of: a first clock for providing timing pulses;

pulse generating means coupled for receiving said timing pulses and for providing in response thereto signals causing the periodic transmission of search pulses into the workpiece;

receiver means coupled for receiving an echo responsive pulse in response to the transmission of a respective search pulse;

timing means coupled for receiving a first signal responsive to the transmission of a search pulse and for subsequently receiving a second signal responsive to the echo responsive pulse associated with said search pulse and generating a timing signal commensurate with the distance traveled by said search pulse in the workpiece during the time interval between said first and second signals;

a second clock for providing periodic clock pulses;

counting means coupled for receiving said periodic clock pulses and for receiving said timing signal and providing in response thereto a third signal in the form of counts commensurate with the quantity of periodic clock pulses occurring during said timing signal;

counter means coupled for receiving said third signal and subsequent third signals for accumulating counts commensurate with the respective quantity of periodic clock pulses occurring during successive timing signals;

programmable counting means coupled to said first clock for receiving said timing pulses and providing a fourth signal when the quantity of said timing pulses received equals a programmed number commensurate with the sound velocity of the workpiece, and readout means coupled to said counter means and said programmable counting means for providing responsive to said fourth signal a readout commensurate with said accumulated counts.

20. An ultrasonic apparatus for measuring as set forth in claim 19, said timing means comprising a flip-flop circuit which is started responsive to said first signal and terminated responsive to said second signal.

21. An ultrasonic apparatus for measuring as set forth in claim 20, and further means coupled to said first clock and said flip-flop circuit for receiving said timing pulses and providing a trigger signal to said flip-flop circuit for starting said flip-flop circuit a predetermined time after receipt of said timing pulse.

22. An ultrasonic apparatus for measuring as set forth in claim 19, and means coupling said timing means to said first clock for periodically resetting said timing means responsive to said timing pulses.

23. An ultrasonic apparatus for measuring as set forth in claim 19, said counting means comprising, a gate coupled to said second clock for receiving at a first input said clock pulses and for receiving at a second input said timing signal; said clock pulses passing through said gate during the time interval between said first and said second signals.

24. An ultrasonic apparatus for measuring as set forth in claim 23, said counting means comprising further a divide by N counter coupled to said gate for providing said third signal responsive to the quantity of said clock pulses passing through said gate.

25. An ultrasonic apparatus for measuring as set forth in claim 19, said programmable counting means comprising an address means and a programmable divide by N counter.

26. An ultrasonic apparatus for measuring as set forth in claim 25, said address means comprising settable switches.

27. An ultrasonic apparatus for measuring as set forth in claim 26, said settable switches being associated with indicia for displaying the sound velocity of the workpiece.

28. An ultrasonic apparatus for measuring as set forth in claim 19, said readout means being a digital display.

29. An ultrasonic apparatus for measuring as set forth in claim 19, said fourth signal being coupled to said counting means and said counter means for periodically resetting said counting means and said counter means.

30. An ultrasonic apparatus for measuring as set forth in claim 19, and a transducer probe means adapted for being coupled to a workpiece coupled to said pulse generating means and said receiver means.

31. An ultrasonic apparatus for measuring as set forth in claim 30, said first signal being en entrant surface responsive echo signal and said second signal being a rear wall responsive echo signal.

32. An ultrasonic apparatus for measuring the thickness of a workpiece by periodically transmitting a search pulse into the workpiece and subsequently receiving echo pulses responsive to the transmission of the search pulse, the combination of:
 a first clock for providing timing pulses;
 pulse generating means coupled for receiving said timing pulses and for providing in response thereto signals causing the periodic transmission of search pulses into the workpiece;
 receiver means coupled for receiving a pair of echo responsive pulses in response to the transmission of a respective search pulse;
 timing means coupled for receiving a first signal being a rear wall responsive echo signal and a second signal being responsive to ultrasonic energy provided by said search signal subsequently intercepting the rear wall of the workpiece and generating a timing signal commensurate with the distance traveled by said search pulse in the workpiece during the time interval between said first and second signals;
 a second clock for providing periodic clock pulses;
 counting means coupled for receiving said periodic clock pulses and for receiving said timing signal and providing in response thereto a third signal in the form of counts commensurate with the quantity of periodic clock pulses occurring during said timing signal;
 counter means coupled for receiving said third signal and subsequent third signals for accumulating counts commensurate with the respective quantity of periodic clock pulses occurring during successive timing signals;
 programmable counting means coupled to said first clock for receiving said timing pulses and providing a fourth signal when the quantity of said timing pulses received equals a programmed number commensurate with the sound velocity of the workpiece, and
 readout means coupled to said counter means and said programmable counting means for providing responsive to said fourth signal a readout commensurate with said accumulated counts.

* * * * *

UNITED STATES PATENT OFFICE
CERTIFICATE OF CORRECTION

PATENT NO. : 3,985,022
DATED : October 12, 1976
INVENTOR(S) : CHRISTOPHER C. DILEO and RICHARD J. PITTARO It is certified that error appears in the above-identified patent and that said Letters Patent are hereby corrected as shown below:

Column 2, line 59, cancel "an" and insert therefor --and--.

Column 4, line 56, cancel "$20^5$" and insert therefor --$10^5$--.

Column 6, line 50, cancel "quentity" and insert therefor --quantity--.

Column 8, line 20, cancel "beng" and insert therefor --being--.

Column 11, line 27, cancel "en" and insert therefor --an--.

Signed and Sealed this

Fourteenth Day of December 1976

[SEAL]

Attest:

RUTH C. MASON
Attesting Officer

C. MARSHALL DANN
Commissioner of Patents and Trademarks